United States Patent
Schantz

(10) Patent No.: US 7,097,646 B2
(45) Date of Patent: Aug. 29, 2006

(54) COLLAPSIBLE ACETABULAR REAMER

(75) Inventor: Eric J. Schantz, Austin, TX (US)

(73) Assignee: Zimmer Inc., Chicago, IL (US)

( * ) Notice: Subject to any disclaimer, the term of this patent is extended or adjusted under 35 U.S.C. 154(b) by 377 days.

(21) Appl. No.: 10/372,366

(22) Filed: Feb. 21, 2003

(65) Prior Publication Data

US 2004/0167528 A1  Aug. 26, 2004

(51) Int. Cl.
*A61B 17/16* (2006.01)
(52) U.S. Cl. ....................................................... 606/81
(58) Field of Classification Search ................ 606/80, 606/81; 366/78, 342–346
See application file for complete search history.

(56) References Cited

U.S. PATENT DOCUMENTS

| 2,571,316 A | * | 10/1951 | Guilder ................ 416/111 |
| 5,658,290 A | * | 8/1997 | Lechot ................. 606/80 |
| 6,755,865 B1 | * | 6/2004 | Tarabishy .............. 623/22.12 |

* cited by examiner

*Primary Examiner*—Eduardo C. Robert
*Assistant Examiner*—D. Jacob Davis
(74) *Attorney, Agent, or Firm*—Williams, Morgan & Amerson, P.C.

(57) ABSTRACT

A method and apparatus for performing minimally invasive hip surgery to implant an acetabular shell into the acetabulum. A collapsible acetabular reamer is moveable between an expanded position and a collapsed position. In the expanded position, the reamer reams the acetabulum. In the collapsed position, the reamer can fit through a small minimally invasive incision.

6 Claims, 4 Drawing Sheets

COLLAPSIBLE ACETABULAR REAMER

FIELD OF THE INVENTION

The disclosure herein generally relates to a method and apparatus for performing minimally invasive hip replacement surgery for the acetabulum using a collapsible acetabular reamer.

BACKGROUND OF THE INVENTION

Traditional hip replacement surgery has been used in the United States since as early as the 1960's. The surgical technique to implant a hip has not drastically changed over the years, and today, this technique is quite successful. In fact, the surgical technique is prolifically used throughout the world and has a known success rate of over 90%. Certainly, the traditional surgical technique is fundamentally sound and predictable.

Unfortunately, traditional techniques to implant a hip have well recognized shortcomings. Most importantly, a rather large incision is made on the side of the hip. The incision can extend from 6 to 12 inches; the actual length of the incision depends on the size of the patient and type of surgery (revision versus total hip arthroplasty, for example). A long, deep incision can divide a number of important stabilizing muscles and tendons and further damage the hip joint and surrounding soft tissue. Inevitably, long incisions lead to larger blood losses, longer rehabilitation times for patients, and unsightly scar lines. A patient can easily spend four or five days in the hospital after a total hip arthroplasty, for example.

Recently, surgeons have been developing new, less invasive surgical techniques to perform total hip arthroplasty and revision hip surgery. Minimally invasive surgery, or MIS, is one such technique with great promise to become a popular and accepted technique for implanting a hip.

MIS has significant advantages over traditional hip replacement surgery. Most importantly, a rather small incision is made on the side on the hip. This incision is approximately 3 to 5 inches long, and the benefits of a shorter incision are enormous.

First and foremost, the patient can recover in a much shorter period of time after a MIS. The recuperation time in the hospital can be a few days and significantly reduce the cost to both the patient and hospital. In fact, some patients are leaving the hospital within 24 to 48 hours after the surgery. Obviously, this shortened time period is extremely important to the patient.

As another advantage, MIS is less invasive and traumatic to the patient. Significantly less soft tissue is disrupted in a minimally invasive surgery compared to a traditional hip surgery. Also, the amount of blood loss is reduced, and patients will require fewer blood transfusions. Further, the length of the scar is significantly smaller, and these scars are more cosmetically appealing. The incisions themselves heal in a much shorter period of time and are much less painful than a long ten or twelve inch incision. As such, the patient can sooner return to work or enjoy recreational activities. In short, the patient can more quickly return to a normal way of life.

Presently, instruments to perform MIS are being developed and refined. These instruments have a vital role in the ability to perform a successful minimally invasive surgery. As one important consideration, these instruments must be able to fit through the small MIS incision. Traditional acetabular reamers are typically hemispherical and have relatively large diameters with deep shell heights. These reamers do not fit well through the small MIS incision.

In short, instruments, and in particular acetabular reamers, play a vital role in MIS surgery for hip implantation. It therefore would be advantageous to provide a new acetabular reamer and method of use for performing a minimally invasive surgery to implant a prosthetic hip.

SUMMARY OF THE INVENTION

The present invention is directed to a method and apparatus for performing minimally invasive hip surgery for the acetabulum using a collapsible acetabular reamer. The collapsible acetabulum reamer of the present invention generally comprises a body having two cutting surfaces. Each cutting surface has a semicircular cutting section and a bridge or mounting section. The cutting surfaces rotate about a common axis and have longitudinal axes that are concentric. The mounting sections extend between the ends of the cutting surfaces and are adapted to connect to a tool driver. Most importantly, the body of the reamer is moveable between two different and distinct positions, a collapsed position and an expanded position. In the expanded position, the body forms a hemispherical shape and the two cutting surfaces are locked together. A tool driver can be attached to the mounting section, and the reamer used to ream the acetabulum. In the collapsed position, the cutting surfaces are unlocked and moved or retracted together. Here, the body no longer forms a hemispherical shape but has more a semi-circular shape. In the collapsed position, the reamer is much smaller and, thus, can more easily fit through a small MIS incision.

Thus, the reamer can physically change its shape back and forth between an expanded position with the body adapted to ream the acetabulum and a collapsed position with the body adapted to pass through a small MIS incision. The movement of the reamer between two different and distinct positions provides numerous advantages over traditional reamers that cannot change shape and size.

The method of the present invention generally comprises the steps of templating the acetabulum to estimate the size of reamer and acetabular components; incising the surgical site with a single incision approximately three inches in length; exposing the acetabular joint and dislocating the hip from the acetabulum; providing a collapsible acetabular reamer; retracting the acetabular reamer to its collapsed position; positioning the reamer through the incision while in the collapsed position; expanding the reamer to its expanded position; reaming the acetabulum with the expanded reamer; retracting the reamer back to its collapsed position; removing the reamer from the incision while in the collapsed position; inserting and aligning an acetabular shell into the reamed acetabulum and impacting the shell into place; inserting and impacting an insert into the shell; and closing the surgical site.

One important advantage of the present invention is that the method and acetabular reamer are used in a minimally invasive orthopedic hip surgery. A single, small three inch incision is made at the surgical site on the side on the hip. The method of the present invention, thus, enjoys the benefits of a shorter incision compared to traditional hip surgery that uses a much longer incision. As one benefit, the patient can recover in a much shorter period of time after a MIS. The recuperation time in the hospital can be a few days and significantly reduce the cost to both the patient and hospital. This shortened time period is extremely important to the patient. Further, MIS is less invasive and traumatic to the patient. Significantly less soft tissue is disrupted in a minimally invasive surgery compared to a traditional hip surgery. Also, the amount of blood loss is reduced, and patients will require fewer blood transfusions. Further, the length of the scar is significantly smaller, and these scars are more cosmetically appealing. The incisions themselves heal in a much shorter period of time and are much less painful than a long ten or twelve inch incision. As such, the patient can sooner return to work or enjoy recreational activities. In short, the patient can more quickly return to a normal way of life.

Another important advantage of the present invention is that a collapsible acetabular reamer is used. This reamer is specifically designed and adapted to be used in minimally invasive surgical techniques for reaming the natural acetabulum of a patient. Specifically, the reamer is moveable back and forth between the collapsed and expanded position. In the expanded position, the reamer has a generally hemispherical shape that is adapted to ream the acetabulum. In the collapsed position, the reamer is much smaller. Here, it has a more semicircular shape. In the collapsed position, the reamer can more easily fit through a small MIS incision.

As another important advantage, since the reamer is readily changeable from the expanded position to the collapsed position, the body or cutting section will not damage or disrupt the sides of the wound channel or surgical site. In the collapsed position, the body of the reamer can easily fit through a small 3–5 inch MIS incision. As such, the body will not disrupt or harm the sides of the incision as the reamer is being placed through the surgical site.

As another advantage, the reamer has a limited number of parts. As such, it can consistently and reliably move between the expanded and collapsed positions. Further, the reamer is not expensive to manufacture.

Further yet, the collapsible reamer is easy to use and facilitates the MIS implantation procedure. As such, the acetabular reamer can appeal to a wide range of orthopedic surgeons with various skills and experience. Further yet, the training and skill level required to use the reamer and become proficient with it is not overly taxing on the orthopedic surgeon.

DETAILED DESCRIPTION

Figure 1:
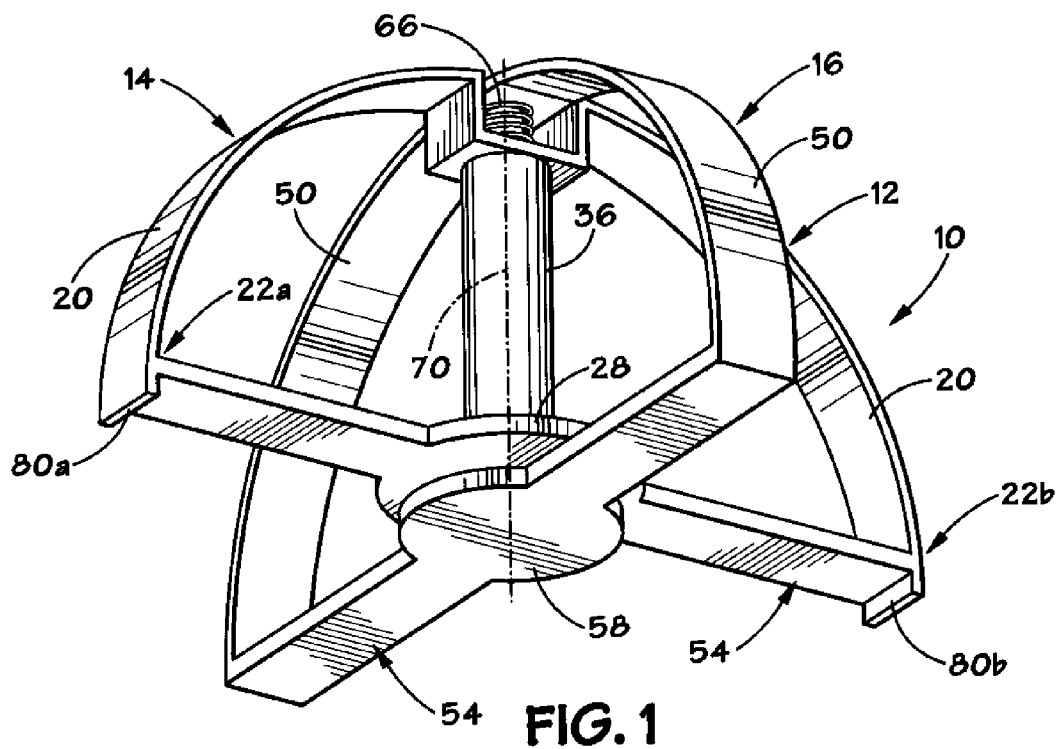
FIG. 1 is a perspective view of a collapsible acetabular reamer in an expanded position according to the invention.

The instruments, method, and steps of the present invention are now described in more detail. The method describes the steps to perform a minimally invasive surgery to implant a prosthetic acetabular component into the natural acetabulum of a patient. Some of these steps described in the method are known to those skilled in the art and will not be discussed in great detail. Further, one skilled in the art will appreciate that certain steps may be altered or omitted while other steps may be added without departing from the scope of the invention. The novel steps of the present invention, for example, can be applied to total hip arthroplasty, to revision surgeries for total and partial hip replacement, and to other orthopedic surgeries using minimally invasive surgical techniques.

To facilitate a discussion of the present invention, the method of implanting a prosthetic acetabular component is divided into a plurality of steps or sections. Each of these sections is discussed seriatim. More specifically, the method of the present invention teaches how to implant a prosthetic acetabular shell and insert into the natural acetabulum using a collapsible acetabular reamer to ream the acetabulum through a small MIS incision. For illustrative purposes, the discussion focuses on implanting a Converge™ Acetabular System of Centerpulse Orthopedics Inc. of Austin, Tex. This system illustrates one possible acetabular system that can be used. One skilled in the art will appreciate that other, different acetabular systems can also be used with the method and apparatus of the present invention without departing from the scope of the invention.

Templating the Acetabulum

Typically, the side of the acetabulum to be reconstructed is templated. Use of a template enables the surgeon to make an estimation of the size of reamers to be used and the size of acetabular component to be inserted. The acetabulum is templated on the both the anterior-posterior (A/P) and lateral radiographs. The hemisphere of the acetabular component is aligned with the mouth of the bony, natural acetabulum while simultaneously avoiding any osteophytes. On the A/P radiograph, the acetabular component should rest on the floor of the cotyloid notch and may touch the illoischial line. Further, the component should have a maximum lateral opening of about 40°. On the groin lateral radiograph, the cup size selected should contact the anterior and posterior rim of the bony, natural acetabulum and the medial subchondral bone. A correct position of the acetabular component will anatomically reproduce the center of rotation of the femoral head. If a bony defect is identified, use the correctly placed template to measure for proper size of the acetabular component and determine any need for bone graft.

Incising the Surgical Site

A relatively small, single minimally invasive incision is made at the surgical site. A minimally invasive incision for this procedure has a length from about 2½ inches to about 4 or 5 inches. The incision is slightly curved or straight, commences near the vastus tubercle, and continues toward the greater trochanter and posterior inferior spine. The incision should be carried down through subcutaneous tissue and fascia lata. Any muscle tissue should be gently split in line with its fibers. Retractors can now be used, as preferred, to retract portions of the site. At this time, a leg length measurement can be taken using techniques known in the art.

Exposing the Acetabular Joint and Dislocating the Hip From the Acetabulum

Next, the knee is flexed, and the leg is internally rotated. Using a hot knife, the piriformis, short external rotators, quadratus femoris, and some posterior capsule are incised off the posterior trochanter to expose the lesser trochanter. Dislocation of the hip can now occur. A bone hook or skid may be used to avoid excess torsion on the femoral shaft.

At this time, retractors may be placed, for example under the femoral head or lesser trochanter, in order to achieve visualization for proper transection of the femoral neck if this procedure is desired at this time. If such transection occurs, the femoral neck should be transected at the templated level. Then retract the femur in an anterior direction to expose the acetabulum. Care should be taken to protect the sciatic nerve.

A retractor can be placed on the pelvis to hold the femur in an anterior position to the acetabulum. The capsule can be retracted in the posterior using retractors or pins. After the labrum and osteophytes are removed, at least a partial view of the acetabulum should be available.

Providing A Collapsible Acetabular Reamer

A collapsible acetabular reamer is provided to ream the natural acetabulum. The reamer is designed and adapted to be used with minimally invasive surgical techniques of the acetabulum. Specifically, the reamer is moveable between an expanded position and a collapsed position. The reamer is more fully discussed in connection with the figures.

Collapsing the Acetabular Reamer

In order to fit easily through the MIS incision, the reamer is retracted to its collapsed position. Specifically, the two cutting surfaces are moved or collapsed toward each other. The body of the reamer, thus, transitions from a generally hemispherical shape to a more semicircular shape. The latter shape is much smaller in size and shape. Once the reamer is collapsed to its smaller size, it is placed through the small MIS incision.

Expanding the Acetabuler Reamer

Once the collapsed reamer is positioned through the incision and into the surgical site, the reamer is expanded. Specifically, the two cutting surfaces are moved or spread apart away from each other and then locked together. The body of the reamer, thus, transitions from a generally semicircular shape back to a hemispherical shape. The reamer is now shaped to ream the acetabulum. Before reaming occurs, the reamer is attached to a tool driver.

Reaming the Acetabulum

Reaming of the acetabulum should begin with a reamer that is two sizes smaller than the preoperatively selected acetabular component size. A smaller reamer ensures that the fit does not exceed the anterior-posterior diameter. Of course, the reamer should not be so small that excessive anterior or posterior reaming occurs. The reamers of the present invention can be made with various sizes to accommodate reaming of the acetabulum.

After an appropriately sized reamer is connected to the driving tool, reaming should begin transversely toward the cotyloid notch. The ridges of the horseshoe (or medial osteophytes) should be removed. Reaming then continues in the position of desired anteversion while simultaneously creating a hemisphere. Larger reamers are used until the anterior and posterior rim of the acetabulum is contacted. The reamer should not be sunk below the superior rim of the bony acetabulum or reamed through the cortical bone of the cotyloid notch. Cancellous bone will be evident where the horseshoe ridges have been removed. The proper size trial shell should be selected according to the size of the reamer.

Collapsing the Acetabular Reamer

After reaming of the acetabulum is complete, the reamer is removed from the surgical site. In order to fit easily through the MIS incision, the reamer is retracted back to its collapsed position. Specifically, the two cutting surfaces are moved or collapsed toward each other. The body of the reamer, thus, transitions from a generally hemispherical shape to a more semicircular shape. Once the reamer is collapsed to its smaller size, it is removed through the small MIS incision and from the surgical site.

Providing An Acetabular Shell Impaction Instrument

An acetabular shell impaction instrument is provided to align and then impact the acetabular shell into the natural acetabulum. The instrument is designed and adapted to be used with minimally invasive surgical techniques of the acetabulum. Specifically, the instrument has a curved shape to fit through the small incision at the surgical site and precisely impact the implanted shell at the correct angular orientation. Further, this curvature enables the instrument to engage the shell in the acetabulum without disrupting the incision and surrounding soft tissue. Further yet, the instrument is adapted to move and align the acetabular shell while it is positioned in the acetabulum. It is important to position properly the shell before it is impacted and permanently seated in the acetabulum.

Inserting an Acetabular Shell Into the Acetabulum

Some acetabular shells may be provided with flared rims and outer bone engaging spikes. In order to insert such a shell, cancellous bone slurry may be added within the acetabulum to fill existing bone cysts and provide an interface layer. Addition of this slurry typically occurs in total hip arthroplasty situations.

The distal connection end of the impaction instrument is engaged and connected to the shell. The shell is partially inserted into the acetabulum until the rim begins to engage bone. The implant is then positioned with the instrument to the desired angular orientation, such as abduction and anteversion. Preferably, the shell is positioned with 20° to 25° of anteversion and with an abduction angle of about 35° to 45°. The anteversion can be verified using techniques known to those skilled in the art. The proximal impaction end of the instrument is then impacted with a mallet or similar instrument. Force from the mallet is transferred from the instrument to the shell as it is driven and permanently seated into the natural acetabulum. The shell should be driven into the acetabulum until the outer fixation spikes centrally engage into cancellous bone.

Removing and Installing Screw-Hole Plugs

The implant shell may be provided with screw-hole plugs, seals, or the like. In this instance, after the shell is properly seated in the acetabulum, one or more of the plugs may be removed with an instrument. Further, the implant shell may be provided with screw-hole plugs or a dome plug that may be installed or inserted into the shell. Typically, these plugs have a head with a tool engaging recess. A threaded shaft extends from the head and is adapted to threadably engage a threaded bore in the acetabular shell.

Drilling Holes and Installing Bone Screws

Next, a drill bit is provided, connected to a flexible driver, and positioned into a selected screw hole. As the hole or bore is drilled, care should be taken to protect the sciatic nerve and superior gluteal artery. A depth gauge may be inserted into the drilled holes to determine the depth for a corresponding bone screw. If desired, a tapping bit may be connected to the driver to tap the hole.

A bone screw is then positioned into the surgical site so the threaded shaft on the bone screw passes through the screw-hole opening in the acetabular shell and into a drilled hole. The bone screw should be seated into the countersunk holes of the shell so the acetabular insert can properly snap into the shell.

Inserting and Impacting an Insert Into the Shell

Various inserts known to those skilled in the art (such as standard, hooded, and protrusion inserts) can be inserted into the implant shell. Once the appropriate size and style insert is selected, the insert is connected to an instrument. The insert is positioned into the cavity of the shell and should be rotated to align with the antirotational pegs on the shell. A surgical mallet is used to strike the proximal end of the instrument to seat the insert into the shell.

Closing Surgical Site

Once the insert is firmly connected to the shell, all instruments and devices are removed from the site. The acetabular shell and insert should now be properly positioned. Closure of the site may occur with well known techniques, such as posterior and anterior lateral approaches. Further, this disclosure will not discuss post-operative protocol or rehabilitation as such procedures are known in the art and tailored to meet the specific needs of the patient.

Detailed Description of Acetabular Reamer

One important advantage of the present invention is that collapsible acetabular reamer is used. This reamer is specifically designed and adapted to be used in minimally invasive surgical techniques for reaming the natural acetabulum of a patient.

Figure 2:
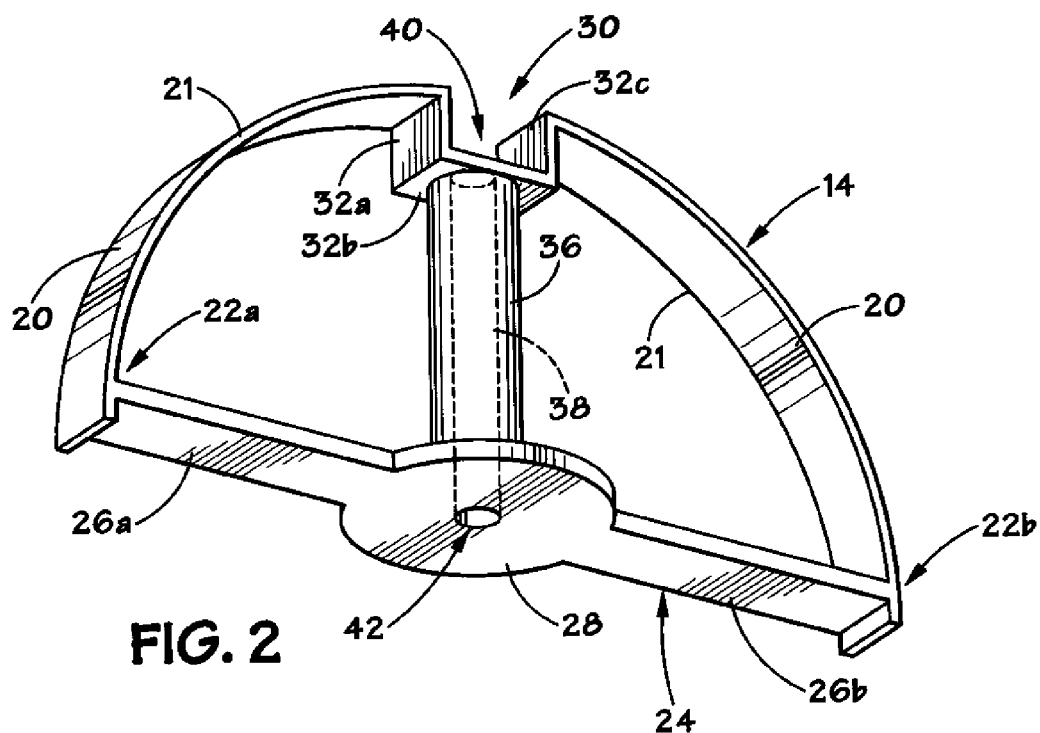
FIG. 2 is a perspective view of the first cutting surface of the collapsible acetabular reamer.
Figure 3:
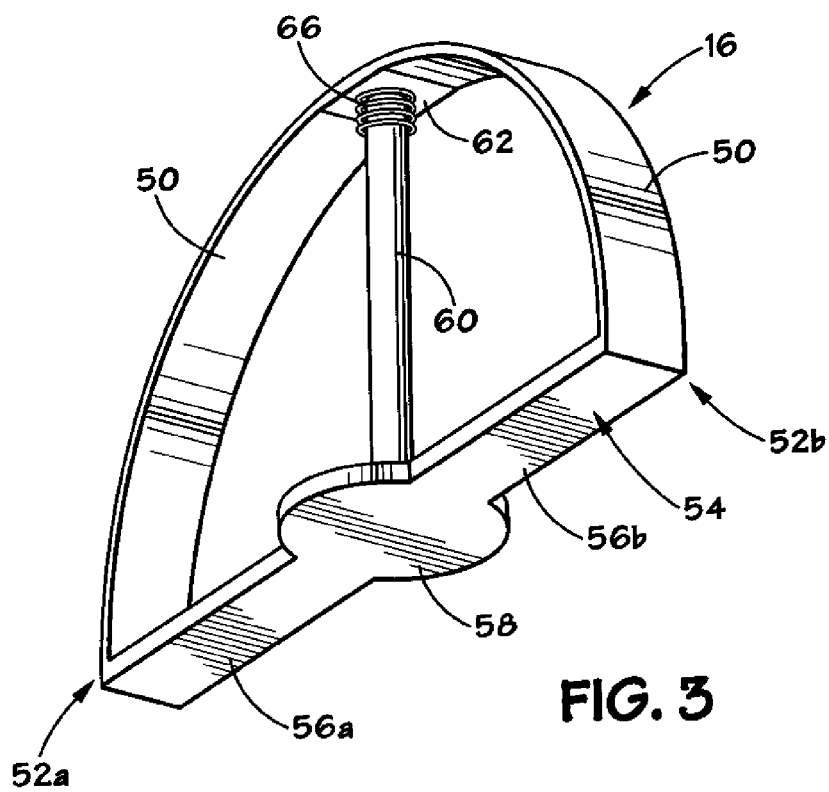
FIG. 3 is a perspective view of the second cutting surface of the collapsible acetabular reamer.

Looking to FIGS. 1–3, the acetabular reamer 10 has a body 12 that includes a first cutting surface 14 and a second cutting surface 16. The first cutting surface 14 includes a semicircular cutting section 20 with edges 21 that are adapted to cut or ream bone, such as the acetabulum of a patient. Cutting section 20 terminates in two ends 22a and 22b. These ends connect to a bridge or mounting section 24. Mounting section 24 has two straight, rectangular base sections 26a and 26b and a centrally located circular hub 28. A capture 30 is formed at the top of the cutting section 20 as a rectangular or square recess. Three rectangular or square surfaces 32a, 32b, and 32c define the recess and capture. An elongated cylindrical post 36 extends between the capture 30 and hub 28. This post has a cylindrical bore 38 with one opening 40 formed through surface 32b in capture 30 and another opening 42 formed through the center of hub 28.

The second cutting surface 16 includes a semicircular cutting section 50 with edges 51 that are adapted to cut or ream bone, such as the acetabulum of a patient. Cutting section 50 terminates in two ends 52a and 52b. These ends connect to a bridge or mounting section 54. Mounting section 54 has two straight, rectangular base sections 56a and 56b and a centrally located circular hub 58. An elongated cylindrical rod 60 extends between a top 62 of cutting section 50 and a center of hub 58. A biasing member 66 is disposed around the rod 60 adjacent the top 62 of cutting section 50. This biasing member may have various configurations known in the art, and is shown as a coiled spring.

When the first and second cutting surfaces are connected, rod 60 is positioned through bore 38. As such, both cutting surfaces are able to rotate about a common longitudinal or central axis 70.

One important advantage of the present invention is that the body 12 of the acetabular reamer 10 is moveable between two different and distinct positions. FIG. 1 shows the first position wherein the body is in an expanded or enlarged state. Here, the first cutting surface 14 and the second cutting surface 16 are perpendicular to each other. In this position, the body has a substantially hemispherical or dome shape. During use, the first cutting surface 14 moves axially or upwardly along longitudinal axis 70. Specifically, post 36 slides upwardly along rod 60, and simultaneously biasing member 66 gets compressed between surface 32b and the underside of cutting surface 16 at top 62. As biasing member 56 gets compressed, cutting surface 16 becomes engaged and locked in capture 30. The cutting surfaces, in this position, are locked together in a hemispherical, expanded shape.

When the cutting surfaces are locked together, the reamer can be used to ream or cut bone. The mounting sections 24 and 54 can be adapted to engage and connect with a driving tool. These driving tools and various connections between the tool and the reamer are known in the art. U.S. Pat. No. 6,250,858 entitled "Tool Driver and Tools Thereof" and U.S. Pat. No. 5,658,290 entitled "Assembly Comprising Reamer Spindle and Reamer for Surgery" teach such driving tools and connections. These two patents are incorporated herein by reference.

Figure 4:
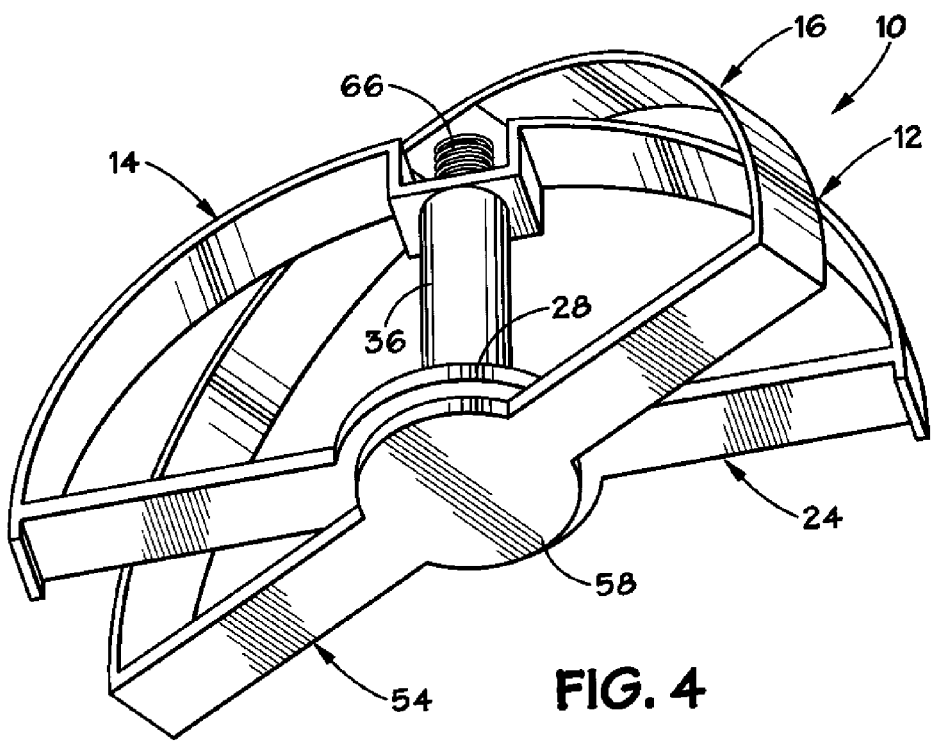
FIG. 4 is a perspective view of the collapsible acetabular reamer in a collapsed position.

FIG. 4 shows the second position wherein the body is in a collapsed or retracted position. Here, the first and second cutting surfaces are generally parallel with each other. In this position, the body has a substantially semicircular shape. In other words, the hemispherical or dome shape has been significantly reduced in size and collapsed to a semicircular shape.

In order to move the reamer from the first position to the second position, the first cutting surface 14 moves axially downwardly along longitudinal axis 70. As post 36 slides down along rod 60, biasing member 66 is uncompressed between surface 32b and the underside of cutting surface 16 at top 62. Capture 30, thus, disengages from cutting surface 16. The two cutting surfaces are unlocked and free to rotate relative to each other about longitudinal axis 70. As such, the cutting surfaces can be rotated until they are substantially parallel with each other. Stop members 80a and 80b may be provided on the ends 22a and 22b, respectively, of cutting section 20 in order to prevent cutting surface 14 from spinning through cutting surface 16.

One important advantage of the present invention is that in the collapsed position, the body of the reamer has a smaller size than in the expanded position. Specifically, the body has been reduced from a hemispherical shape to a generally semicircular shape. The latter shape is smaller and easier to fit through a small MIS incision. Thus, the reamer can physically change its shape back and forth between an expanded position with the body adapted to ream the acetabulum and a collapsed position with the body adapted to pass through a small MIS incision. The movement of the reamer between two different and distinct positions provides numerous advantages over traditional reamers that cannot change shape and size.

Figure 5:
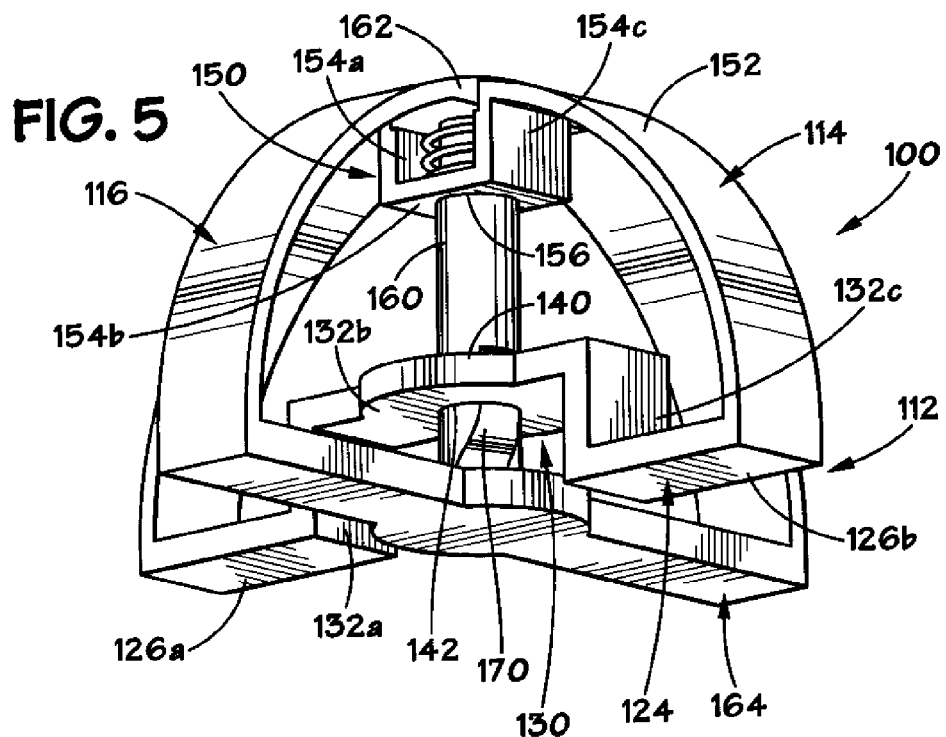
FIG. 5 is a perspective view of an alternate embodiment of the collapsible acetabular reamer in an expanded position.
Figure 6:
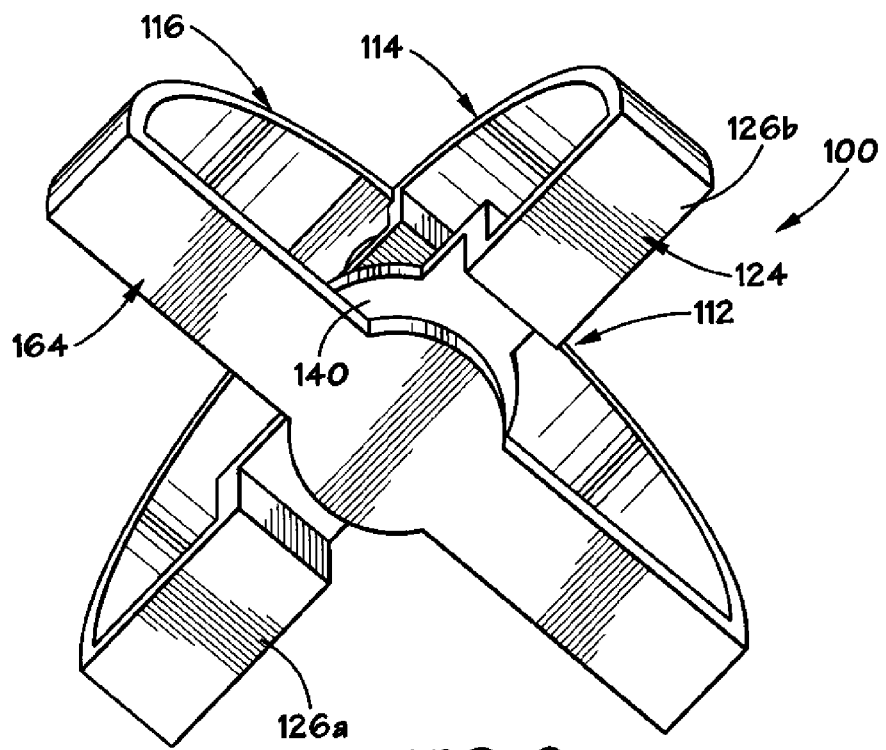
FIG. 6 is a bottom perspective view of the reamer of FIG. 5.
Figure 7:
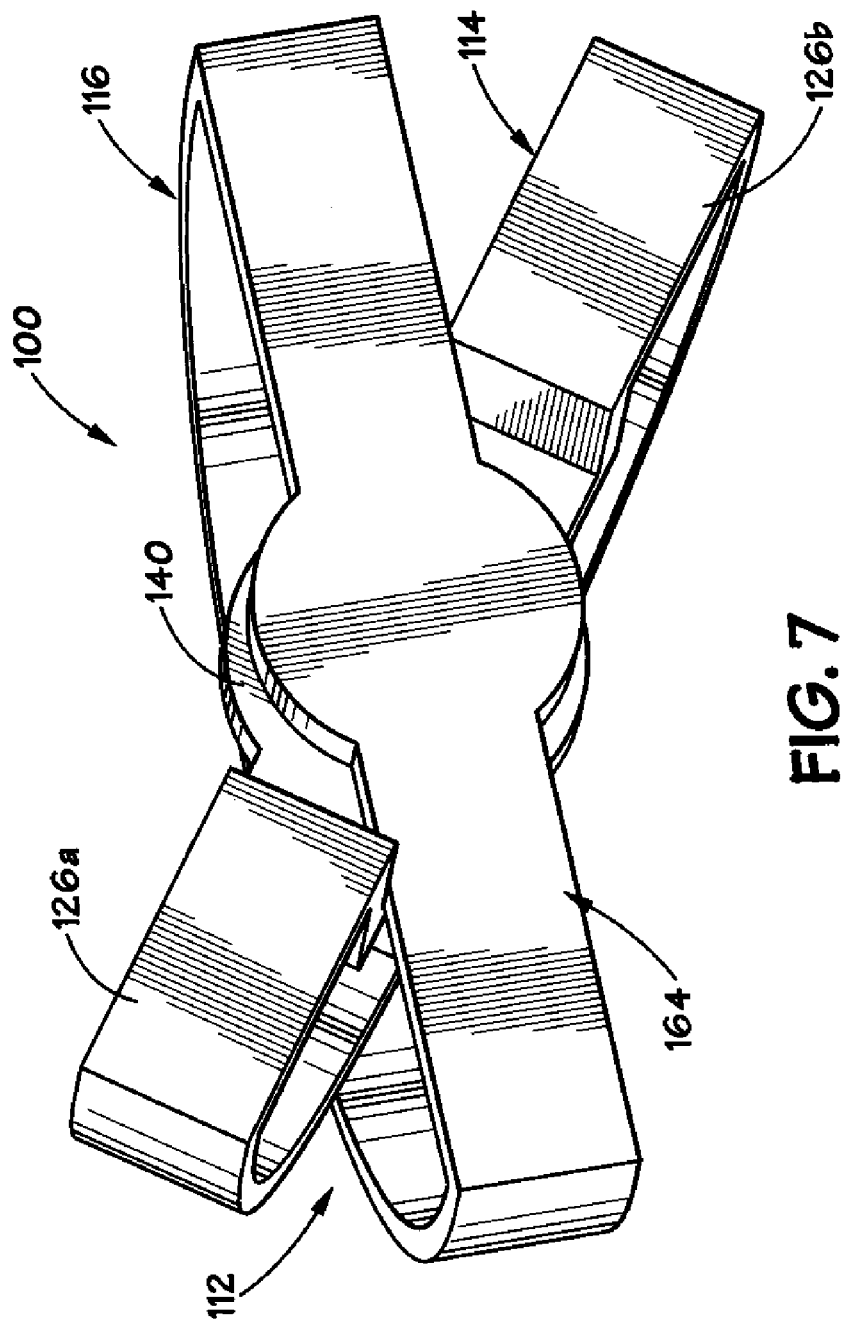
FIG. 7 is a bottom view of the reamer of FIG. 5 in a collapsed position.

After reading this disclosure, one skilled in the art will appreciate that the body of the reamer can be altered and still be within the scope of the invention. Various embodiments can be used to create an acetabular reamer that is moveable between two positions in order to more readily fit through small MIS incisions. FIGS. 5–7 show one such embodiment.

FIGS. 5–7 show an acetabular reamer 100 that is similar to the reamer 10 discussed in connection with FIGS. 1–4. As such, only significant differences between these two reamers will be discussed.

Reamer 100 has a body 112 that includes a first cutting surface 114 and a second cutting surface 116. These cutting are similar to the cutting surfaces 14 and 16. As one difference, cutting surface 114 includes a mounting section 124 with two straight, rectangular base sections 126a, 126b and a capture 130. The capture is formed as a rectangular or square recess and is defined with three surfaces, 132a, 132b, and 132c. Surface 132b includes a central, circular hub 140.

A cylindrical bore 142 extends through the hub 140. Another capture 150 is oppositely disposed from capture 130. Capture 150 is formed along cutting section 152 as a rectangular or square recess defined with three surfaces 154a, 154b, and 154c. Surface 154b includes a bore 156 that aligns with bore 142.

Cutting surface 116 includes a rod 160 that extends between cutting section 162 and mounting section 164. This rod is positioned through bores 142 and 156 to connect the first and second cutting surfaces. Further, one end of the rod 160 can include a twisted guide channel or cut 170. This cut rotationally guides or twists the first and second cutting surfaces to and from the collapsed and expanded positions. More particularly, FIGS. 5 and 6 show the body 112 in a hemispherical or expanded position, and FIG. 7 shows the body in a substantially semicircular or collapsed position.

The acetabular reamers of the present invention have been shown in use to ream a natural acetabulum of a patient. One skilled in the art will appreciate that the reamers of the present invention can be utilized in other surgical indications as well. For example, the reamers can be adapted to be used to ream or cut bone for a MIS knee surgery, shoulder surgery, or other MIS surgeries that require a reamer.

It should be emphasized that although the method of the present invention was described with a specific number and sequence of steps, these steps can be altered or omitted while other steps may be added without departing from the scope of the invention. As such, the specific steps discussed in the preferred embodiment of the present invention illustrate just one example of how to utilize the novel method and steps of the present invention. Further, although illustrative embodiments and methods have been shown and described, a wide range of modifications, changes, and substitutions is contemplated in the foregoing disclosure and in some instances, some features of the embodiments or steps of the method may be employed without a corresponding use of other features or steps. Accordingly, it is appropriate that the appended claims be construed broadly and in a manner consistent with the scope of the embodiments disclosed herein.

What is claimed is:

1. A method for using minimally invasive surgery to ream a natural acetabulum in a patient, comprising the steps of:
   incising a hip with a minimally invasive incision;
   providing an acetabular reamer attachable to a driving tool, the reamer having a body that is adjustable to a first position with a first shape that is a substantially hemispherical shape and to a second position with a second shape that is substantially semicircular;
   positioning the reamer to the second position and second shape;
   inserting the reamer through the minimally invasive incision while in the second position;
   positioning the reamer from the second position to the first position and first shape;
   reaming the natural acetabulum while the reamer is in the first position;
   positioning the reamer from the first position to the second position and second shape;
   removing the reamer from the minimally invasive incision while in the second position; and
   closing the incision.

2. The method of claim 1, wherein the step of incising a hip creates the minimally invasive incision with a length of about 2½ inches to about 4 to 5 inches.

3. The method of claim 1, further comprising the step of providing the second shape to be smaller than the first shape.

4. The method of claim 3, further comprising the step of enlarging the reamer to perform the step of positioning the reamer from the second position to the first position.

5. The method of claim 3, further comprising the step of reducing a size of the reamer to perform the step of positioning the reamer from the first position to the second position.

6. The method of claim 1, further comprising the steps of collapsing the reamer to perform the step of positioning the reamer from the first position to the second position, and expanding the reamer to perform the step of positioning the reamer from the second position to the first position.

* * * * *